United States Patent [19]

Schromm et al.

[11] 3,950,335

[45] Apr. 13, 1976

[54] 1-(3'-TRIFLUOROMETHYL-4'-CHLORO-PHENYL)-2-AMINO-PROPANES AND SALTS THEREOF

[75] Inventors: Kurt Schromm; Ernst-Otto Renth; Anton Mentrup; Richard Reichl, all of Ingelheim am Rhine, Germany

[73] Assignee: Boehringer Ingelheim GmbH, Ingelheim am Rhein, Germany

[22] Filed: June 11, 1974

[21] Appl. No.: 478,264

Related U.S. Application Data

[63] Continuation-in-part of Ser. No. 138,002, April 27, 1971, abandoned.

[30] Foreign Application Priority Data

May 2, 1970 Germany............................ 2021620

[52] U.S. Cl............ 260/253; 260/326 R; 260/343.7; 260/455 A; 260/471 C; 260/501.18; 260/501.19; 260/562 B; 260/562 N; 260/570.5 C; 260/570.8 R; 260/646; 424/253; 424/280; 424/300; 424/324; 424/330
[51] Int. Cl.².................. C07C 97/10; C07D 473/00
[58] Field of Search...... 260/570.5 C, 570.8 R, 253, 260/343.7, 501.18

[56] References Cited
UNITED STATES PATENTS

| 3,198,834 | 8/1965 | Beregi et al................. 260/570.8 R |
|---|---|---|
| 3,337,626 | 8/1967 | Thiele et al................ 260/501.18 X |
| 3,504,028 | 3/1970 | Beregi et al.............. 260/570.8 R X |
| 3,683,008 | 8/1972 | Beregi et al.................. 260/570.6 X |
| 3,759,979 | 9/1973 | Beregi et al................. 260/553 A X |
| 3,829,469 | 8/1974 | Thiele et al.............. 260/570.8 R X |

FOREIGN PATENTS OR APPLICATIONS

| 230,869 | 11/1963 | Austria......................... 260/570.8 R |
|---|---|---|
| 1,528,540 | 6/1968 | France.......................... 260/570.8 R |

*Primary Examiner*—Robert V. Hines
*Assistant Examiner*—Thomas A. Waltz
*Attorney, Agent, or Firm*—Hammond & Littell

[57] ABSTRACT

Compounds of the formula

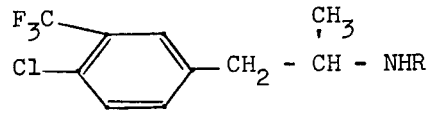

wherein
R is $-(CH_2)_n - CO - C_6H_5$; $-(CH_2)_n - CO - CH_3$
where
$n$ is 1 or 2, or $-CO - R_1$
where
$R_1$ is ethoxy, ethylthio, chloromethyl, aminomethyl or, benzylaminomethyl;
and non-toxic, pharmacologically acceptable acid addition salts thereof; the compounds as well as their salts are useful as appetite suppressants.

4 Claims, No Drawings

1-(3'-TRIFLUOROMETHYL-4'-CHLORO-PHENYL)-2-AMINO-PROPANES AND SALTS THEREOF

This is a continuation-in-part of copending application Ser. No. 138,002, filed Apr. 27, 1971, now abandoned.

This invention relates to a novel class of 1-(3'-trifluoromethyl-4'-chloro-phenyl)-2-aminoalkanes and non-toxic, pharmacologically acceptable acid addition salts thereof, as well as to various methods of preparing these compounds.

More particulary, the present invention relates to a racemic mixture of a compound of the formula $$F_3C-\text{C}_6H_3(Cl)-CH_2-CH(CH_3)-NHR \quad (I)$$

wherein
R is $-(CH_2)_n - CO - C_6H_5$; $-(CH_2)_n - CO - CH_3$,
where
$n$ is 1 or 2, or $-CO-R_1$
where
$R_1$ is ethoxy, ethylthio, chlormethyl, aminomethyl, or benzylaminomethyl;
an optically active component thereof; or a non-toxic pharmacologically acceptable acid addition salt of said racemate or optically active component.

A particularyl preferred subgenus of the compounds according to the present invention are those of the formula $$F_3C-\text{C}_6H_3(Cl)-CH_2-CH(CH_3)-NHR$$

wherein
R is $-CH_2 - CO - C_6H_5$, $-CH_2 - CO - CH_3$ $-CO-R_1$
where
$R_1$ is ethoxy, benzylaminomethyl or aminomethyl;
and non-toxic, pharmacologically acceptable acid addition salts thereof.

The compounds of the invention may be prepared in any convenient way. According to a further feature of the invention they may be prepared by treating a compound of the formula $$F_3C-\text{C}_6H_3(Cl)-CH_2-CH(CH_3)-NH_2 \quad (II)$$

with alkylatin or acylating agents of the general formula $$R - Y \quad III.$$

in which R has the meaning mentioned above and Y is a radical which may be split off as an anion, for example a halogen atom or the radical of a suitable sulphonic acid such as toluene or methanesulphonic acid.

Where the radical R is a group $-(CH_2)_2 - CO - C_6H_5$ or $-(CH_2)_2 - CO - CH_3$, this may introduced by the conditions of the Mannich-reaction.

Racemic mixtures of a compound of the formula I may, if desired, be resolved into optically active components thereof by conventional methods, such as by fractional precipitation with an optically active acid, followed by liberation of the optionally active base.

The compounds embraced by formula 1, in the racemic as well as optically active forms, are organic bases and therefore form acid addition salts with inorganic or organic acids by known methods. Examples of non-toxic, pharmacologically acceptable acid addition salts are those formed with hydrochloric acid, sulfuric acid, phosphoric acid, tartaric acid, ascorbic acid, 8-chlorotheophylline or the like.

The starting compounds may be prepared by conventional processes, or in analogous fashion, as illustrated by the reaction sequence below.

Thus, condensation of a substituted benzaldehyde (IV) with nitroethane yields a nitro-olefin of the formula V, from which an amine of the formula II is obtained by reduction with a complex metal hydride, such as lithium aluminum hydride:

$$F_3C-\text{C}_6H_3(X)(R_1)-C(CH_3)=O + H_2C-NO_2 \longrightarrow$$

$$F_3C-\text{C}_6H_3(X)(R_1)-C(CH_3)=C-NO_2 \quad (V)$$

The following examples further illustrate the present invention and will enable others skilled in the art to understand it more completely. It should be understood, however, that the invention is not limited solely to the particular examples given below.

EXAMPLE 1

Ethyl 4-chloro-3-trifluoromethyl-α-methyl-phenethylcarbonate 3.3 gm of ethyl chloroformate were added dropwise to a mixture consisting of 7 gm of 1-(4'-chloro-3'-trifluoromethyl-phenyl)-2-amino-propane, 4 gm of sodium carbonate and 50 ml of acetonitrile, and the resulting mixture was heated for 15 mintues at 40°C and then stirred for 12 hours at room temperature. Thereafter, the reaction mixture was vacuum-filtered, and the filtrate was evaporated. The residual oil was dissolved in ether, the resulting solution was shaken with dilute hydrochloric acid, the ether phase was separated and evaporated, and the residue was fractionally distilled, yielding ethyl 4-chloro-3-trifluoromethyl-α-methylphenyl-carbamate, b.p. 135°–140°C at 0.35 mm Hg, of the formula $$F_3C-\text{C}_6H_3(Cl)-CH_2-CH(CH_3)-NHCOOC_2H_5$$

which had a melting point of 56°–58°C after recrystallization from petroleum ether. In an analogons manner the ethyl-4-chloro-3-trifluoromethyl-α-methylphenethyl-thiocarbamat m.p. 67°C may be produced.

EXAMPLE 2

1-(4'-chloro-3'-trifluoromethyl-phenyl)-2-(β-chloroacetylamino)-propane 1-(4'-chloro-3'-trifluoromethyl-phenyl)-2-aminopropan was reacted with chloroacetylchlorid in acetonitril to form 1-(4'-chloro-3'-trifluoromethyl-phenyl)-2-(β-chloroacetyl-amino)-propan

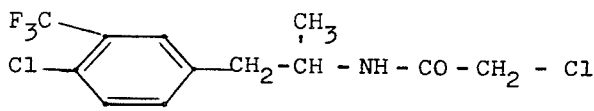

which had a melting point of 59°–63°C after recristallisation.

EXAMPLE 3

1-(4'-Chloro-3'-trifluoromethyl-phenyl)-2-[(β-benzylaminoacetyl)-amino]-propane hydrochloride A mixture consisting of 12.6 gm of 1-(4'-chloro-3'-trifluoromethyl-phenyl)-2-(β-chloroacetylamino)-propan, 100 ml of acetonitrile and 9.4 gm of benzylamine was refluxed for two hours. Thereafter, the precipitated benzylamine hydrochloride was filtered off, the acetonitrile was evaporated from the filtrate, and the residue, 1-(4'-chloro-3'-trifluoromethyl-phenyl)-2-[(β-benzylamino-acetyl)-amino]-propane, was taken up in ethyl acetate. The resulting solution was washed with water, then acidified with ethereal hydrochloric acid, and the precipitate formed thereby was collected and recrystallized from water yielding the compound of the formula

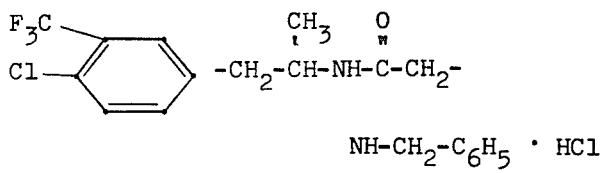

having a melting point of 161°–164°C.

EXAMPLE 4

1-(4'-Chloro-3'-trifluoromethyl-phenyl)-2-(β-aminoacetylamino)-propane and its methanesulfonate 1-(4'-Chloro-3'-trifluoromethyl-phenyl)-2-(β-chloroacetyl-amino)-propane was reacted with potassium phthalimide in dimethyl formaide at 100°C to form 1-(4'-chloro-3'-trifluoromethyl-phenyl)-2-[(β-phthalimido-acetyl)-amino-propane. A mixture consisting of 16 gm of this product, 250 ml of ethanol and 3.8 gm of hydrazine hydrate was refluxed for one hour. Thereafter, the resulting reaction solution was acidified with glacial acetic acid, cooled and vacuum-filtered, and the filtrate was evaporated. The residue was dissolved in water, the resulting aqueous solution was vacuum-filtered through charcoal, the filtrate was made alkaline with ammonia and was then extracted with ethyl acetate. and the organic extract solution was washed with water, dried and evaporated. The residue, 1-(4'-chloro-3'-trifluoromethyl-phenyl)-2-(β-aminoacetyl-amino)-propane, was dissolved in acetonitrile, the resulting solution was acidified with methanesulfonic acid, and the precipitate formed thereby was collected and rectystallized form ethanol, yielding the compound of the formula

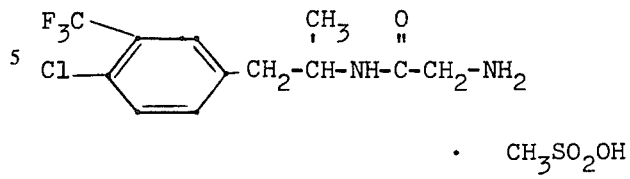

having a melting point of 193°–196°C.

EXAMPLE 5

1-(4'-Chloro-3'-trifluoromethyl-phenyl)-2-(phenacyl-amino)-propane and its hydrochloride A mixture consisting of 23.8 gm of 1-(4'-chloro-3'-trifluoromethyl-phenyl)-2-amino-propane, 9.3 gm of α-bromoacetophenone and 100 ml of acetonitrile was stirred for 30 minutes and then evaporated. Ether was added to the residue, the resulting mixture was vacuum-filtered, and the filtrate was evaporated. The residue, 1-(4'-chloro-3'-trifluoromethyl-phenyl)-2-(phenacyl-amino)-propane, was dissolved in acetonitrile, the resulting solution was acidified with ethereal hydrochloric acid, and the precipitate formed thereby was collected and recrystallized form methanol/water, yielding the compound of the formula

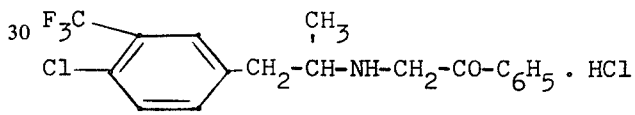

having a melting point of 210°–213°C.

EXAMPLE 6

1-(4'-Chloro-3'-trifluoromethyl-phenyl)-2-(acetonylamino)-propane and its hydrochloride 2.53 ml of chloroacetone were added dropwise to a boiling mixture consisting of 6.45 gm of 1-(4'-chloro-3'-trifluoromethyl-phenyl)-2-amino-propane, 50 ml of acetonitrile and 2.93 gm of sodium carbonate, and the mixture was refluxed for one hour. Thereafter, the reaction mixture was vacuum-filtered, the filtrate was evaporated, and the residue, 1-(4'-chloro-3'-trifluoromethyl-phenyl)-2-(acetonyl-amino)-propane, was dissolved in ethyl acetate. The resulting solution was acidified with ethereal hydrochloric acid, and then ether was added, and the precipitate formed thereby was collected and recrystallized form isopropanol, yielding the compound of the formula

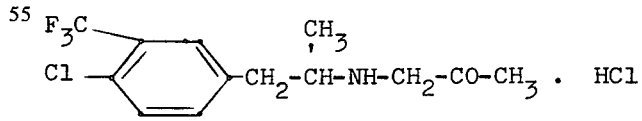

having a melting point of 191°–194°C.

The compounds of the present invention, that is, racemates or optically active compounds embraced by formula I and their non-toxic, pharmacologically acceptable acid addition salts, have useful pharmacodynamic properties. More particularly, the compounds of the instant invention exhibit very effective anorectic activities with extremely low central nervous system stimulating side effects and very low toxicity in warm-blooded animals, such as rats.

For pharmaceutical purposes the compounds according to the present invention are administered to warm-blooded animals perorally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups and the like. One effective anorectic dosage unit of the compounds according to the present invention is from 0.0166 to 0.83 mgm/kg body weight, preferably 0.041 to 0.167 mgm/kg body weight.

The following examples illustrate a few peroral dosage unit compositions comprising a compound of the present invention as an active ingredient and represent the best modes contemplated of putting the invention into practical use. The parts are parts by weigh unless otherwise specified.

EXAMPLE 7

Tablets

The tablet composition was compounded from the following ingredients:

| | | |
|---|---|---|
| Ethyl 4-chloro-3-trifluoromethyl-α-methyl-phenethyl carbamate | 5.0 | parts |
| Lactose | 262.0 | " |
| Polyvinylpyrrolidone | 3.0 | " |
| Corn starch | 27.0 | " |
| Colloidal silicic acid | 2.0 | " |
| Magnesium stearate | 1.0 | " |
| Total | 300.0 | parts |

PREPARATION

The phenyl-aminopropane compound was intimately admixed with the lactose, the corn starch and the colloidal silicic acid; the resulting mixture was moistened with an aqueous solution of the polyvinylpyrrolidone; the moist mass was granulated by passing it through a 1.5 mm-mesh screen; the granulate was dried at 40°C; the dry granulate was again passed through the screen and was then admixed with the magnesium stearate, and the resulting composition was compressed into 300 mgm-tablets in a conventional tablet-making machine. Each tablet contained 5 mgm of the phenylaminopropane compound and was a peroral dosage unit composition with effective anorectic action.

EXAMPLE 8

Coated Pills

The pill core composition was compounded from the following ingredients:

| | |
|---|---|
| 1-(4'-Chloro-3'-trifluoromethyl-phenyl)-2-[(β-benzylaminoacetyl)-amino]-propane hydrochloride | 10.0 parts |
| Lactose | 257.0 parts |
| Polyvinylpyrrolidone | 3.0 parts |
| Corn starch | 27.0 parts |
| Colloidal silicic acid | 2.0 parts |
| Magnesium stearate | 1.0 parts |
| Total | 300.0 parts |

Preparation

The ingredients were compounded as described in Example 5, the finished composition was compressed into 300 mgm-pill cores, and the pill cores were coated in conventional manner with a thin shell consisting essentially of a mixture of sugar, talcum, gum arabic, titanium oxide and polyvinylpyrrolidone. Each coated pill contained 10 mgm of the phenyl-aminopropane compound and was a peroral dosage unit composition with effective anorectic action.

EXAMPLE 9

Wafer Capsules

The capsule filler composition was compounded from the following ingredients:

| | | |
|---|---|---|
| 1-(4'-Chloro-3'-trifluoromethyl-phenyl)-2-(phenacyl-amino)-propane hydrochloride | 2.5 | parts |
| Lactose, crystalline | 77.5 | " |
| Talcum | 20.0 | " |
| Total | 100.0 | parts |

Preparation

The phenyl-aminopropane compound was passed through a 0.75 mm-mesh screen and was then intimately and uniformly admixed with the lactose and the talcum, and 100 mgm-portions of the resulting composition were filled into wafer capsules of suitable size. Each capsule contained 2.5 mgm of the phenyl-aminopropane compound and was a peroral dosage unit composition with effective anorectic action.

Analogous results were obtained when any one of the other compounds embraced by formula I or a non-toxic, pharmacologically acceptable acid addition salts thereof was substituted for the particular phenyl-aminopropane in Examples 5 through 7. Likewise, the amount of active ingredient in these illustrative examples may be varied to achieve the dosage unit range set forth above, and the amounts and nature of the inert pharmaceutical carrier ingredients may be varied to meet particular requirements. Moreover, a dosage unit composition comprising a compound according to the present invention may, in addition, contain an effective dosage unit of another type of active ingredient, such as laxative.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A racemic mixture of a compound of the formula

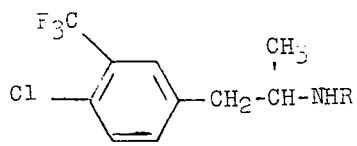

wherein
R is $-(CH_2)_n-CO-C_6H_5$ or $-(CH_2)_n-CO-CH_3$,
where
$n$ is 1 or 2,
an optically active component thereof; or a non-toxic, pharmacologically acceptable acid addition salt of said racemate or optically active component.

2. A compound of claim 1,
wherein R is
—CH₂—CO—C₆H₅ or —CH₂—CO—CH₃, or a non-toxic, pharmacologically acceptable acid addition salt thereof.

3. A compound of claim 2, which is 1-(4'-chloro-3'-trifluoromethyl-phenyl)-2-(acetonyl-amino)-propane or a non-toxic, pharmacologically acceptable acid addition salt thereof.

4. A compound of claim 2, which is 1-(4'-chloro-3'-trifluoromethyl-phenyl)-2-(phenacyl-amino)-propane or a non-toxic, pharmacologically acceptable acid addition salt thereof.

* * * * *